United States Patent [19]

Dawe

[11] 3,998,223
[45] Dec. 21, 1976

[54] SYRINGE APPARATUS
[75] Inventor: Albert Rolke Dawe, Deerfield, Ill.
[73] Assignee: The United States of America as represented by the Secretary of the Navy, Washington, D.C.
[22] Filed: Oct. 24, 1975
[21] Appl. No.: 625,393
[52] U.S. Cl. .............................. 128/218 P; 128/234
[51] Int. Cl.² ............................................ A61M 5/00
[58] Field of Search ...... 128/218 P, 218 PA, 218 R, 128/218 M, 215, 216, 220, 272, 236, 173, 237, 235; 222/386, 340

[56] References Cited
UNITED STATES PATENTS

| 1,308,919 | 7/1919 | Sellar | 128/215 |
|---|---|---|---|
| 1,476,946 | 12/1923 | Bessesen | 128/218 P |
| 2,650,591 | 9/1953 | Love | 128/218 R X |
| 3,295,525 | 1/1967 | Evers et al. | 128/272 |

FOREIGN PATENTS OR APPLICATIONS

| 1,058,902 | 4/1902 | France | 128/218 P |

Primary Examiner—John D. Yasko
Attorney, Agent, or Firm—R. S. Sciascia; George A. Montanye

[57] ABSTRACT

A modified hand-held syringe suitable for medical and biological purposes having a disposable resilient balloon-like diaphragm for advantageously assuring the delivery of fluid at a more even pressure than that attained by thumb pressure applied to a non-modified syringe. Moreover, the balloon-like structure simultaneously acts as an indicator of excessively applied pressure. Clinically, the device is particularly suited for use with patients having athlerosclorosis, or other diseases affecting cardio-vascular walls. Also, proper use of the device precludes excessive hematoma. In other laboratory and research contexts, the device is particularly suited for the administration of liquid to delicate tissues.

3 Claims, 4 Drawing Figures

U.S. Patent    Dec. 21, 1976    3,998,223
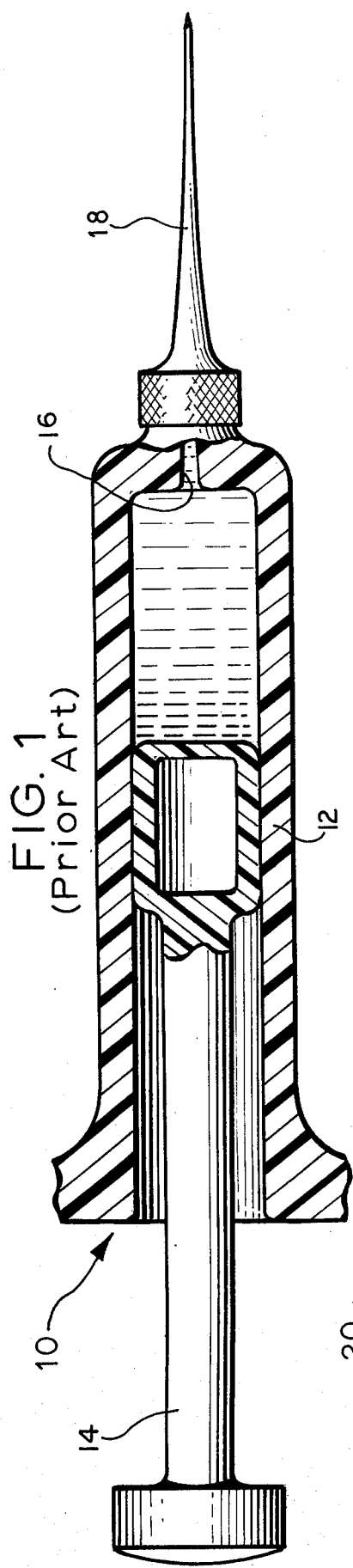
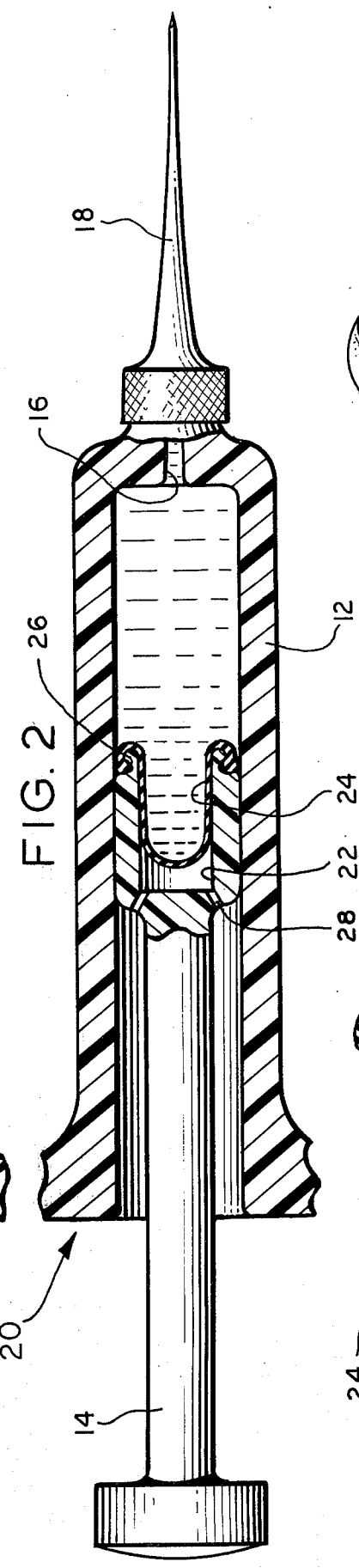
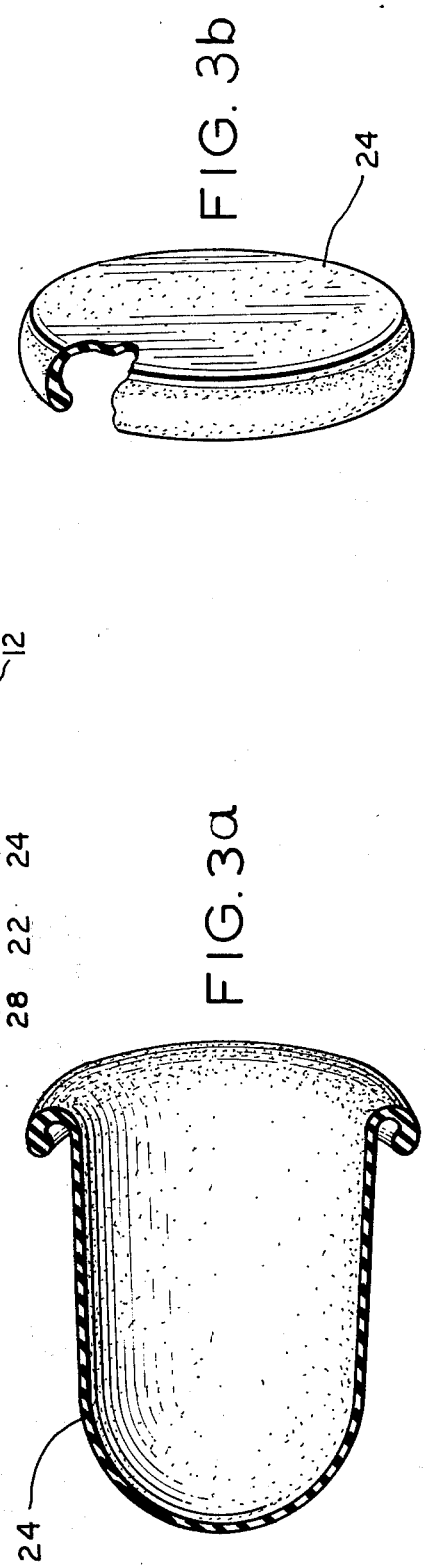

SYRINGE APPARATUS

The invention described herein may be manufactured and used by or for the Government of the United States of America for governmental purpose without the payment of royalty thereon or therefore.

BACKGROUND OF INVENTION

This invention relates to the class of devices for the administration of substances in a liquid medium and more particularly to a hand-held, finger-operated hypodermic syringe.

Various devices including the hypodermic syringe have been successfully employed over the past decades for the administration of substance into organs, animals, and human beings. The common spring consists of a needle, plunger, and barrel, and has proven satisfactory in that the damage sustained by the target due to the puncture is de minimis and the subsequent increase in pressure as a result of the liquid injection does not deleteriously affect the living tissue in the surrounding area. That is to say the surrounding tissue is usually able to sustain the increased pressure which pressure is proportional to that applied to the plunger. If the plunger is depressed with a quick swift push, the fluid is delivered at a high pressure. As the plunger is depressed in a jerky, uneven manner, the fluid pressure through the needle will fluctuate and be irregular. Although such actions will in most cases do little harm to the target, those sufferring from cardiovascular diseases or other diseases whose characteristics include the weakening of vessel walls must be treated with care. Accordingly, any substance applied to such patients must be done so that even pressure and maximum care be taken not to exascerbate the tissue near the area of the injection. Moreover, even through the hypodermic injection causes no permanent harm to patients without cardiovascular diseases, the irregular application of pressure or the excess of it can cause hematoma and is quite painful. In the laboratory many examples are also available to show the need to evenly apply liquid substances in a delicate manner.

When treating diseases with the characteristics cited above, or use of the device as previously stated, the application of a substance at high or fluctuating pressure as delivered by a hypodermic injection, may create undesirable stress on tissue in the immediate area or further degrade the walls of a system. As a matter of fact, serious thought is often given to the decision regarding whether or not an afflicted patient or a delicate organ should be subjected to the risk of the injection itself.

Accordingly, with the above drawbacks in mind, I have developed a device which is capable of evening the applied pressure during a hypodermic injection so as to reduce the risks of inflecting harm to a patient or organ. Moreover, I have invented an inexpensive hypodermic syringe device which is capable of indicating the amount of pressure provided to the patient in combination with a pressure relief mechanism.

It is, therefore, a primary object of the present invention to provide a hypodermic syringe device capable of indicating the amount of pressure applied through its needle and into the patient or organ.

Another object of this invention is to provide a hypodermic syringe device capable of simultaneously controlling and indicating the pressure applied through the needle. Other objects, advantages and novel features of the invention will become apparent from the following detailed description taken in conjunction with the accompanying drawing wherein:

FIG. 1 is a longitudinal sectional of the typical hand-held, finger-operated hypodermic syringe known to the prior art;

FIG. 2 is a longitudinal sectional view of my hand-held, finger operating syringe modified in accordance with the teachings of this invention;

FIG. 3(a) depicts the balloon-like structure required to practice this invention in its expanded condition;

FIG. 3(b) depicts it in its normal condition.

SUMMARY

A typical hand-held, finger-operated hypodermic syringe is modified to provide a reduction of short pressure bursts and to even-out the pressure applied through the needle thereof. To this end, the plunger portion of the syringe is modified to accommodate a balloon-like resilient structure in lieu of the typical flat plunger end section known to the prior art. When finger pressure is applied to the plunger, the resilient balloon-like structure expands. If the pressure in the needle section is higher than a threshold amount, this expansion indicates to the operator that consideration should be given to the removal and replacement of the needle. Also the resiliency of the balloon-like structure provides an even fluid flow through the needle, substantially irrespective of the applied finger pressure.

DETAIL DESCRIPTION

Referring to FIG. 1, prior art, a well known hand-held syringe is provided. This syringe can be and is of various sizes, lengths, and proportions. The syringe consists of barrel 12 which is usually calibrated to show the amount of fluid in it. Usually, barrel 12 is made of glass or other light transmissible substance, including Lucite. The innerwall is usually machined smooth as to provide a leak-proof slideable fit with plunger 14. Plunger 14 is also tubular of a smaller diameter and forces any liquid inside barrel 12 through hole 16 when finger pressure is applied. A significant pressure is developed by the application of finger pressure. As a consequence, fluid located inside barrel 12 progresses through needle 18 at a pressure dependent upon the pressure applied to plunger 14. As stated previously, the unevenness of the applied pressure is not advantageous, and a significant amount of tissue damage can be realized at the orifice of the needle without being detected by the finger.

FIG. 2, depicts a syringe modified in accordance with the teachings of the present invention.

Similar to the structure shown in FIG. 1, the modified device 20 has a barrel 12, needle opening 16 and needle 18.

The modification is effected at the plunger 14. Specifically in lieu of the flat disc shape and as known in the prior art, the device is equipped with an annular lip 26 and hole 22 on which is mounted a disposable balloon like structure 24. Balloon like 24 is shown in its expanded condition.

Also vent hole 28 is provided at the extreme end so that air is vented therethrough when the same is displaced by the expansion of the balloon-like member.

Balloon-like structure 24 resembles rubber condom in resilience and shape, as shown in its expanded condition of FIG. 3(a). Although the selection of the particular balloon-like structure substantially depends upon the size of the needle orifice, the length of the needle, and the viscosity of the substance administered, it is believed that the rubber available from various condom manufacturers is generally satisfactory.

As shown in FIG. 2 and FIG. 3(a), the expanded balloon-like structure is removable and disposable. Also to provide the ability to pull the plunger back, an annular ridge should be provided around the end of the structure as shown in FIG. 3(b).

Obviously many modifications and variations of the present invention are possible in the light of the above teachings. It is therefore to be understood that within the scope of the appended claims the invention may be practiced otherwise than as specifically described.

I claim:

1. In a hand-held hypodermic syringe for the administration of a fluid, the syringe having a needle, a slideable plunger for applying a pressure to the fluid, and a barrel, the improvement comprising:

resilient means disposed within the slideable plunger for controlling pressure through the needle; and venting means in the slideable plunger for permitting free movement of the resilient means.

2. An improved hypodermic syringe comprising:

a needle having an annular hole through the center thereof;

a rigid barrel having an opening in abuttable engagement with the annular hole in the needle;

a plunger slideably disposed in the rigid barrel, said plunger having an annular lip around a tubular section at an end thereof; including a resilient balloon like structure, a resilient balloon like structure adapted to be fitted over the annular lip around the tubular section of the plunger.

3. The improved hypodermic syringe of claim 2 wherein:

venting means are provided to the tubular section of plunger for assuring free movement of the resilient structure.

* * * * *

UNITED STATES PATENT AND TRADEMARK OFFICE
CERTIFICATE OF CORRECTION

PATENT NO. : 3,998,223
DATED : December 21, 1976
INVENTOR(S) : Albert R. Dawe

It is certified that error appears in the above-identified patent and that said Letters Patent are hereby corrected as shown below:

Column 4, line 12, cancel "a" and insert --said--.

Signed and Sealed this

Twelfth Day of April 1977

[SEAL]

Attest:

RUTH C. MASON
Attesting Officer

C. MARSHALL DANN
Commissioner of Patents and Trademarks